(12) United States Patent
Donner et al.

(10) Patent No.: US 9,795,419 B2
(45) Date of Patent: Oct. 24, 2017

(54) SPINAL STABILIZATION SYSTEM

(71) Applicant: JCBD, LLC, Fort Collins, CO (US)

(72) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 0 days.

(21) Appl. No.: 15/408,157

(22) Filed: Jan. 17, 2017

(65) Prior Publication Data

US 2017/0119440 A1    May 4, 2017

Related U.S. Application Data

(63) Continuation of application No. 15/332,947, filed on Oct. 24, 2016, now Pat. No. 9,603,638, which is a continuation of application No. 14/209,138, filed on Mar. 13, 2014, now Pat. No. 9,510,872.

(60) Provisional application No. 61/794,543, filed on Mar. 15, 2013.

(51) Int. Cl.
    *A61B 17/70*    (2006.01)
(52) U.S. Cl.
    CPC ...... *A61B 17/7049* (2013.01); *A61B 17/7032* (2013.01); *A61B 17/7071* (2013.01)
(58) Field of Classification Search
    CPC .................. A61B 17/7049; A61B 17/7032
    See application file for complete search history.

(56) References Cited

U.S. PATENT DOCUMENTS

| | | | | |
|---|---|---|---|---|
| 2002/0116000 A1* | 8/2002 | Zucherman | ............ | A61K 31/37 606/249 |
| 2002/0147449 A1* | 10/2002 | Yun | ..................... | A61B 17/7062 606/249 |
| 2005/0033434 A1* | 2/2005 | Berry | ................. | A61B 17/7064 623/17.14 |
| 2005/0131409 A1* | 6/2005 | Chervitz | ............. | A61F 2/30771 606/247 |
| 2006/0217718 A1* | 9/2006 | Chervitz | ............ | A61B 17/7064 606/247 |
| 2006/0224159 A1* | 10/2006 | Anderson | .......... | A61B 17/7062 606/248 |
| 2006/0241601 A1* | 10/2006 | Trautwein | .......... | A61B 17/7049 606/248 |
| 2007/0162000 A1* | 7/2007 | Perkins | .............. | A61B 17/7062 606/249 |

(Continued)

FOREIGN PATENT DOCUMENTS

KR    WO2007052975 A1    5/2007

*Primary Examiner* — Ellen C Hammond
*Assistant Examiner* — Stuart S Bray
(74) *Attorney, Agent, or Firm* — Glenn H. Lenzen; Dietze and Davis, P.C.

(57) ABSTRACT

A spinal stabilization system and method are provided for treating a patient's spinal column, for maintaining preselected spacing and movement between adjacent vertebrae in a spinal column, and for providing overall stability thereto. The system includes an interlaminar member positioned in the space intermediate a first vertebra and the vertebrae positioned immediately below and adjacent to the first vertebra. The interlaminar member is operatively connected to an adjustable support structure and cooperates therewith to maintain the preselected spacing between adjacent vertebrae and to provide overall stability to the spinal column.

17 Claims, 13 Drawing Sheets

(56) References Cited

U.S. PATENT DOCUMENTS

| | | | |
|---|---|---|---|
| 2007/0233068 A1* | 10/2007 | Bruneau | A61B 17/7067 623/17.11 |
| 2007/0233129 A1* | 10/2007 | Bertagnoli | A61B 17/1604 606/79 |
| 2008/0015609 A1* | 1/2008 | Trautwein | A61B 17/7062 606/99 |
| 2008/0228225 A1* | 9/2008 | Trautwein | A61B 17/1606 606/246 |
| 2008/0269904 A1* | 10/2008 | Voorhies | A61B 17/7026 606/86 A |
| 2008/0281361 A1* | 11/2008 | Vittur | A61B 17/7052 606/249 |
| 2008/0306549 A1 | 12/2008 | Winslow | |
| 2009/0018662 A1* | 1/2009 | Pasquet | A61B 17/7008 623/17.16 |
| 2009/0024169 A1* | 1/2009 | Triplett | A61B 17/1757 606/248 |
| 2009/0138048 A1* | 5/2009 | Baccelli | A61B 17/8869 606/263 |
| 2009/0149885 A1* | 6/2009 | Durward | A61B 17/7067 606/246 |
| 2009/0187217 A1* | 7/2009 | Weiman | A61B 17/7052 606/257 |
| 2009/0204151 A1* | 8/2009 | Bracken | A61B 17/7049 606/246 |
| 2009/0216276 A1* | 8/2009 | Pasquet | A61B 17/7043 606/249 |
| 2009/0270920 A1* | 10/2009 | Douget | A61B 17/7055 606/254 |
| 2010/0049252 A1* | 2/2010 | Smisson, III | A61B 17/7049 606/250 |
| 2010/0069965 A1* | 3/2010 | Abdou | A61B 17/7064 606/279 |
| 2011/0071568 A1* | 3/2011 | Ginn | A61B 17/7062 606/249 |
| 2011/0106163 A1* | 5/2011 | Hochschuler | A61B 17/7062 606/264 |
| 2011/0106257 A1* | 5/2011 | Matge | A61F 2/442 623/17.11 |
| 2011/0137345 A1* | 6/2011 | Stoll | A61B 17/7049 606/251 |
| 2011/0160772 A1* | 6/2011 | Arcenio | A61B 17/7053 606/248 |
| 2011/0218571 A1* | 9/2011 | Attia | A61B 17/7062 606/248 |
| 2012/0065683 A1* | 3/2012 | Kuo | A61B 17/7062 606/248 |
| 2012/0078303 A1* | 3/2012 | Malek | A61B 17/7067 606/250 |
| 2012/0130427 A1* | 5/2012 | Hoffman | A61B 17/7055 606/248 |
| 2012/0136390 A1* | 5/2012 | Butler | A61B 17/7067 606/248 |
| 2012/0150228 A1* | 6/2012 | Zappacosta | A61B 17/7068 606/248 |
| 2012/0158060 A1* | 6/2012 | Abrahams | A61B 17/7052 606/248 |
| 2012/0215262 A1* | 8/2012 | Culbert | A61B 17/1606 606/279 |
| 2012/0226312 A1* | 9/2012 | Thalgott | A61B 17/7062 606/246 |
| 2012/0226314 A1* | 9/2012 | Chin | A61L 27/425 606/249 |
| 2013/0023933 A1* | 1/2013 | Haas | A61B 17/7065 606/248 |
| 2013/0030467 A1* | 1/2013 | Karas | A61B 17/686 606/248 |
| 2013/0053854 A1* | 2/2013 | Schoenefeld | A61B 17/1757 606/87 |
| 2013/0296939 A1* | 11/2013 | Perkins | A61B 17/7068 606/249 |
| 2013/0345753 A1* | 12/2013 | Kretzer | A61B 17/7049 606/248 |
| 2014/0074166 A1* | 3/2014 | Scarrow | A61B 17/7067 606/247 |
| 2014/0316467 A1* | 10/2014 | Siegal | A61B 17/7062 606/249 |
| 2015/0012040 A1* | 1/2015 | Agarwal | A61B 17/7068 606/248 |

* cited by examiner

SPINAL STABILIZATION SYSTEM

CROSS-REFERENCE TO RELATED APPLICATIONS

This application is a continuation of U.S. patent application Ser. No. 15/332,947, filed Oct. 24, 2016, which is a continuation of U.S. patent application Ser. No. 14/209,138, filed Mar. 13, 2014, which claims the benefit of U.S. Provisional Application No. 61/794,543, filed Mar. 15, 2013; the entire disclosures of which are incorporated herein by reference.

FIELD OF THE INVENTION

The present invention relates generally to the field of medical apparatus and methods for using the same. More specifically, the present invention relates to systems and methods for treating spinal conditions, and specifically for systems for stabilizing vertebrae in the spinal column. More specifically, the present invention relates to interlaminar vertebral stabilization devices for placement between adjacent vertebra and including supporting devices for stabilization of the vertebral segments above and below the vertebra being treated.

BACKGROUND OF THE INVENTION

Injury to and/or diseases of the spine frequently result in damage to or abnormalities in the vertebrae, the intervertebral discs, the facet joints and to the connective tissue and ligaments around the spine. Such damage or abnormalities may result in spinal instability causing misalignment of the vertebral column and wear of the intervertebral discs and vertebral bony surfaces, a chronic and progressive deterioration which typically results in severe pain, loss or restriction of motion, and eventually, loss of mobility of the individual suffering from the condition.

One treatment option for addressing spinal disorders is via surgical intervention and the placement of fusion, stabilization and/or repair devices on or adjacent to the spine or between adjacent vertebrae. Certain surgical procedures are irreversible, for example, fusion techniques using bone grafts or synthetic implants to fuse vertebra, and may also significantly alter vertebral range of motion. Other procedures, for example procedures for installing spinal implants or pedicle screw systems for fixating two or more vertebrae, are intricate, time consuming and highly invasive. Alternative solutions include the insertion of interspinous or intralaminar spacers in the space between adjacent vertebrae to control relative motion between and to stabilize the two vertebrae. However, the stabilization does not extend above or below the insertion point, leaving the remaining portions of the spinal column subject to unstable motion and the potential damage resulting therefrom.

Various prior art systems have attempted to address the problems described above. U.S. Pat. No. 5,645,599 issued to Samani on Jul. 8, 1997 (the '599 patent), discloses an interspinal implant device having a generally u-shaped, spring-like configuration for insertion between the spinal processes of adjacent vertebrae. Samani's device includes opposing pairs of upwardly and downwardly extending brackets adapted to be secured to the spinal process, thereby providing for flexible positioning of the adjacent vertebrae. However, the apparatus of the '599 patent does not attribute to the overall stability of the spinal column; its effect being limited to the two specific vertebrae to which it is attached. It is also difficult to attach multiple devices configured in accordance with Samani's disclosure at adjacent segments due to interference of the bracket portions.

Hochschuler et al disclose various intra-laminar stabilization systems in U.S. Patent Application Publication No. US 2009/0204150 published on Aug. 13, 2009 (the '150 publication), and in U.S. Patent Application Publication No. US 2011/0106163 published on May 5, 2011 (the '163 publication). The '150 publication discloses a pair of oppositely disposed hook members that are translationally positioned on a rod and adapted to engage the laminar regions of adjacent vertebra and maintain a preselected spacing there between. However, the apparatus of the '150 publication does not stabilize other vertebrae in the spinal column, its effect being limited to the two adjacent vertebrae which it engages.

The Hochschuler et al. '163 publication discloses an interlaminar stabilizing system which includes a structure adapted to be disposed between two adjacent vertebrae as described above with respect to the apparatus of the '150 publication. The '163 structure further includes a support structure which is secured to the second vertebra to further restrict the interval spacing between the adjacent vertebrae. However, the system of the '163 disclosure also does not stabilize the vertebrae in the remaining portions of the spinal column for the reasons set forth above.

Moreover, none of the known prior art systems address the problem of "transition syndrome" or "adjacent segment disease" associated with fusion of adjacent vertebrae. In fusion, if a motion segment is eliminated via fusion, the unfused adjacent segments above and below the fused vertebrae take up and bear the additional forces induced by bending and rotational movement of the spine, which may result in so-called "transition syndrome" over the long term. In addition, none of the prior art systems provide for augmenting previously installed spinal hardware to enhance stability, adjust intervertebral distraction, and so forth.

Accordingly, a need exists for an improved spinal stabilization system which provides both flexibility and stability to the spinal column and which addresses the combination of problems not solved by the prior art.

SUMMARY OF THE INVENTION

The stated problems and other needs in the art as apparent from the foregoing background may be addressed in accordance with the systems and methods of the present invention as set forth in various embodiments disclosed herein.

In an embodiment, an improved spinal stabilization system is provided for maintaining preselected spacing and movement between adjacent vertebrae and also for providing overall stability to the spinal column.

In one embodiment, a spinal stabilization system is provided which includes at least one interlaminar member adapted to be inserted between two adjacent vertebrae and a stabilizing structure for stabilizing the vertebrae at least one layer above and below the two adjacent vertebrae.

In another embodiment, a spinal stabilization system is provided which includes a blocking member to limit movement of adjacent vertebrae to prevent narrowing of the spinal canal and nerve compression.

In yet another embodiment, a spinal stabilization system is provided which includes at least one adjustable cross-linking member to enhance stability of the spine.

In still another embodiment, a method for treating a patient's spinal column is disclosed employing at least one of the embodiments of the spinal stabilization system of the present invention.

These and other features of the present invention will be apparent from the accompanying description of the invention, diagrams and supplemental supporting materials provided herein.

DESCRIPTION OF THE INVENTION

It should be noted that the present description is by way of illustration only, and that the concepts and examples presented herein are not limited to use or application with any single system or methodology. Hence, while the details of the system and methods described herein are for the convenience of illustration and explanation with respect to the exemplary embodiments, the principles disclosed may be applied to other types of spinal stabilization systems without departing from the scope of the present invention.

Figure 1:
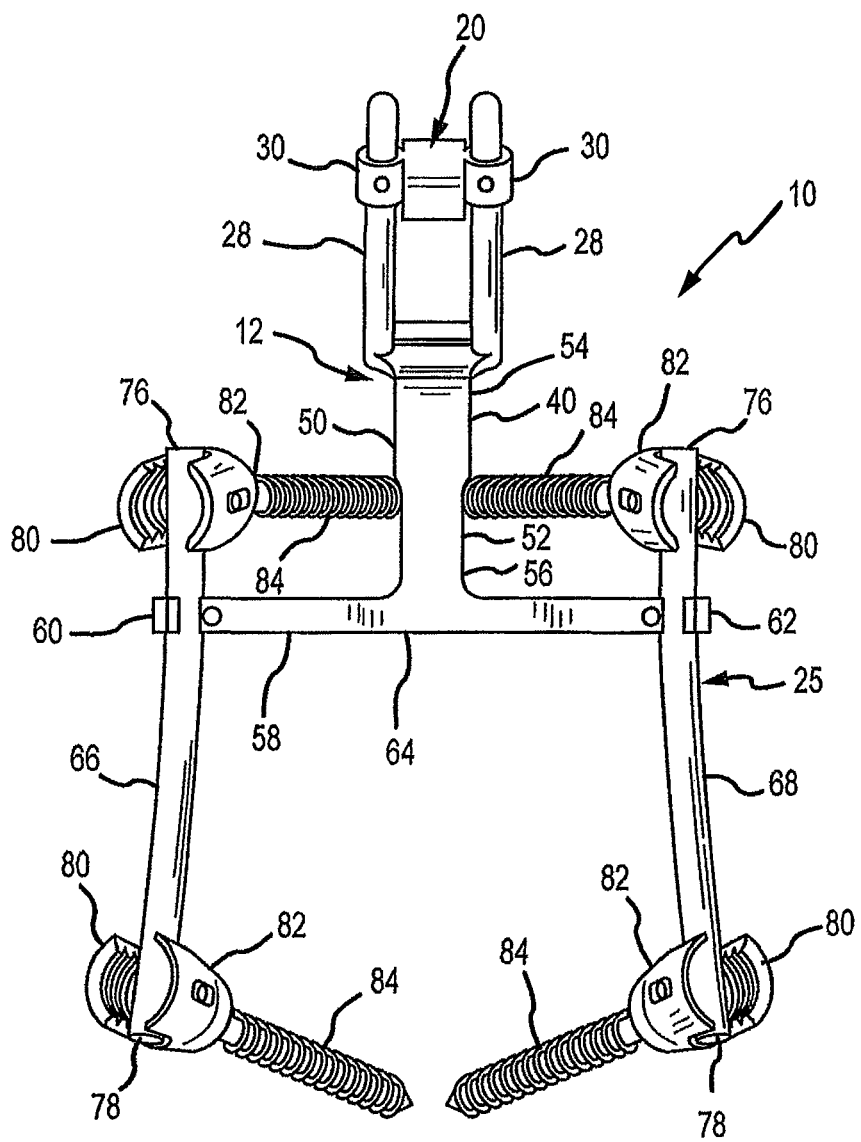
FIG. 1 is a front plan view of a spinal stabilization system of the present invention.
Figure 2:
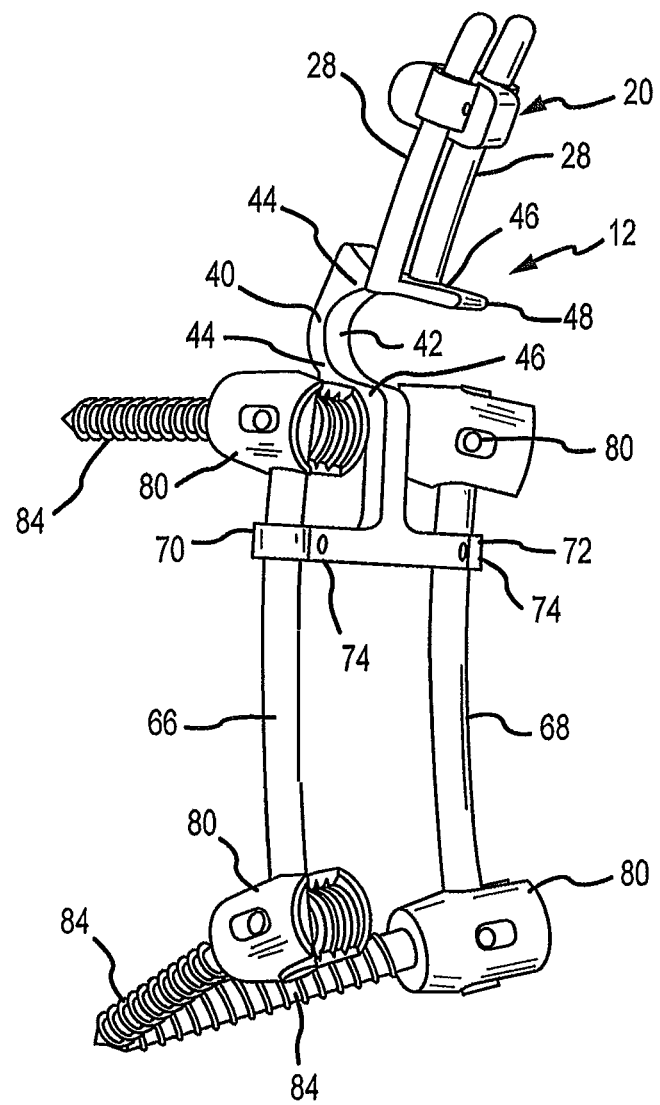
FIG. 2 is a side perspective view of a spinal stabilization system of the present invention.
Figure 3:
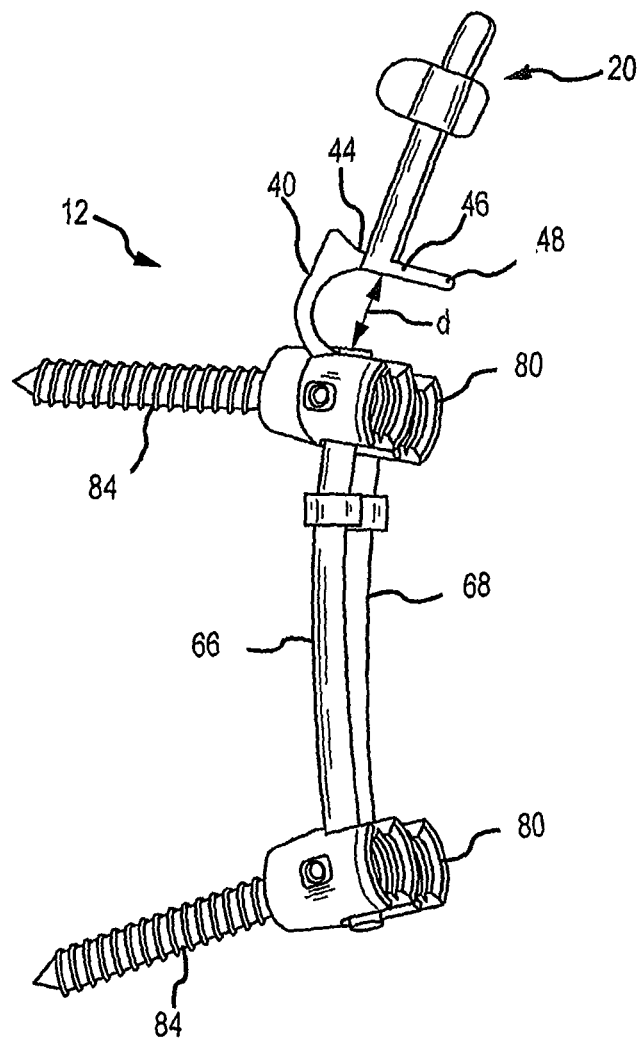
FIG. 3 is a side plan view of a spinal stabilization system of the present invention.
Figure 4:
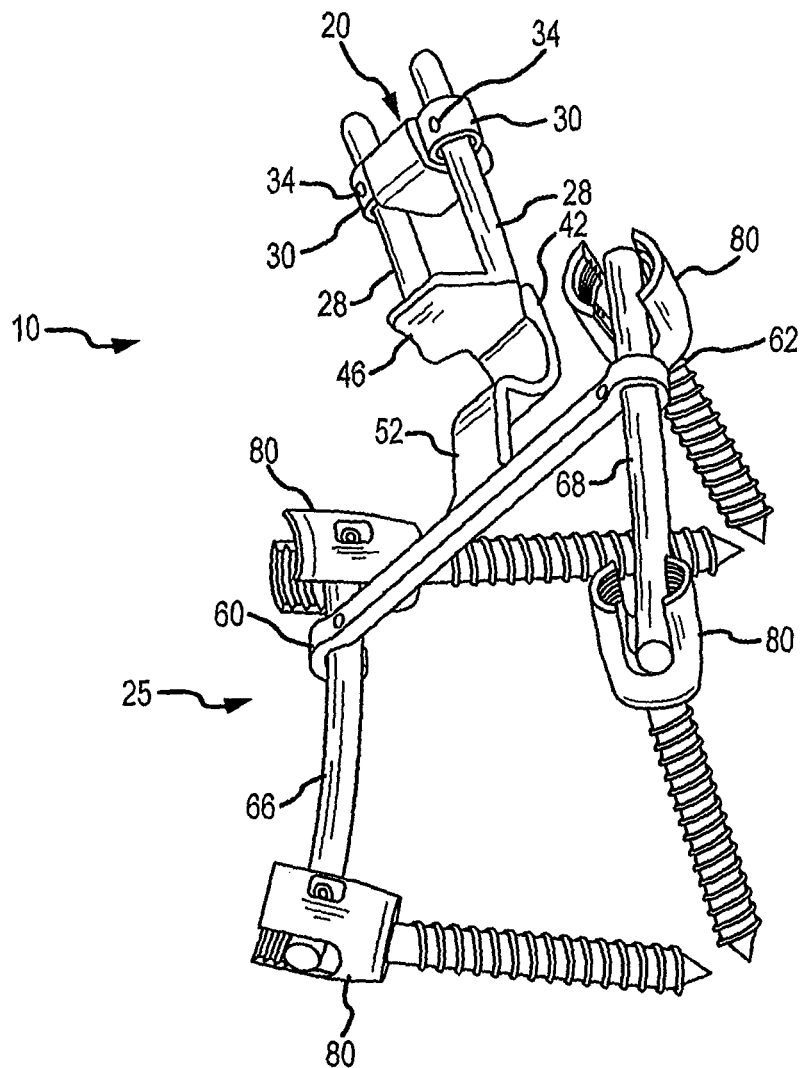
FIG. 4 is a bottom perspective view of a spinal stabilization system of the present invention.
Figure 5:
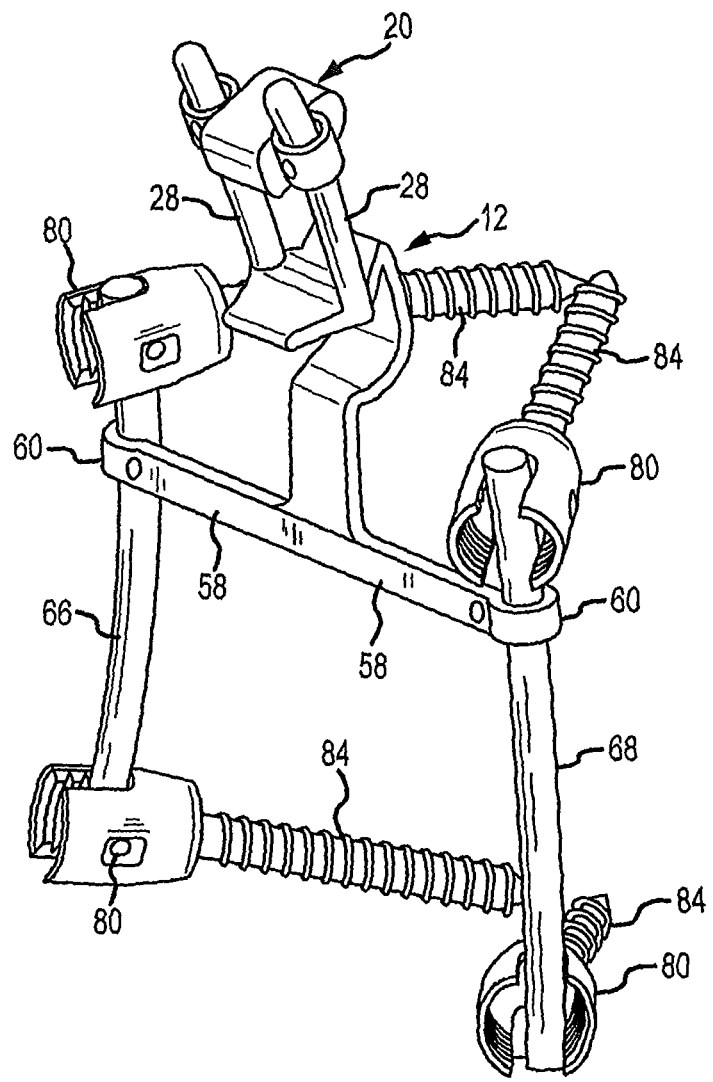
FIG. 5 is a top perspective view of a spinal stabilization system of the present invention.

Referring now to FIG. 1, a spinal stabilization system according to an embodiment of the present invention is shown generally at 10 (which for purposes of brevity will be referred to herein as "the system"). The system includes a first interlaminar member 12 adapted to be positioned between adjacent vertebra in a spinal column. As shown in greater detail in FIGS. 6 and 7, the interlaminar member 12 is shown positioned between a first vertebra 14 and a second adjacent vertebra 16 in a spinal column 18.

The system further includes a second interlaminar member 20 adapted to be positioned between the second vertebra 16 and a third vertebra 22 in the spinal column 18. Both the first and second interlaminar members are operatively connected to a support structure shown generally at numeral 25 in FIG. 1. By way of example, in the embodiment shown, the support structure and the first interlaminar member are integrally formed from a single piece of material such as titanium or stainless steel suitable for use as a medical implant device. However, it is to be understood that other means for connecting the interlaminar device to the support structure such as hinges, pins, threaded fasteners and the like may also be used without departing from the scope of the invention.

Figure 9:
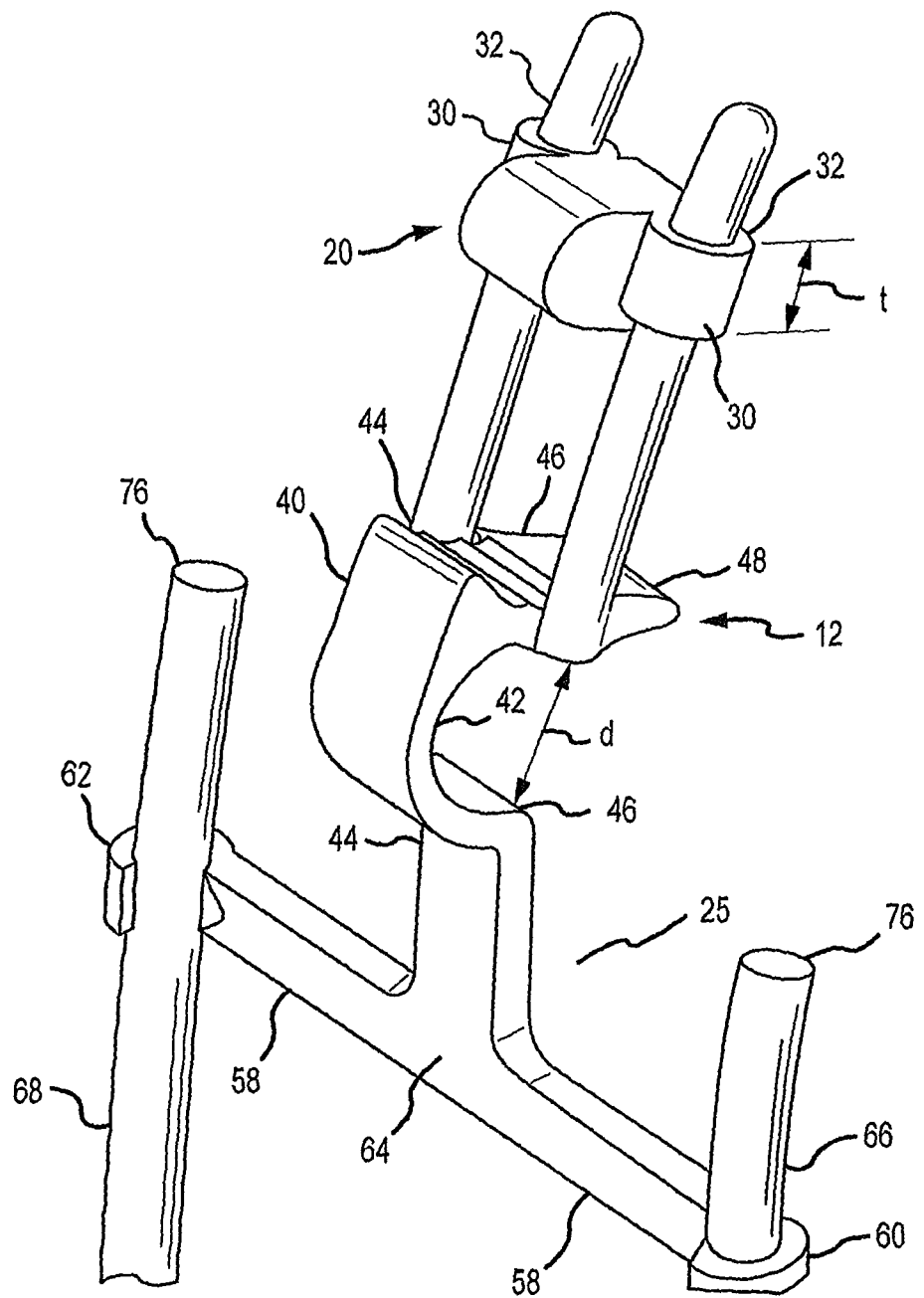
FIG. 9 is an exploded rear perspective view of a portion of the spinal stabilization system shown in FIGS. 6, 7 and 8.
Figure 10:
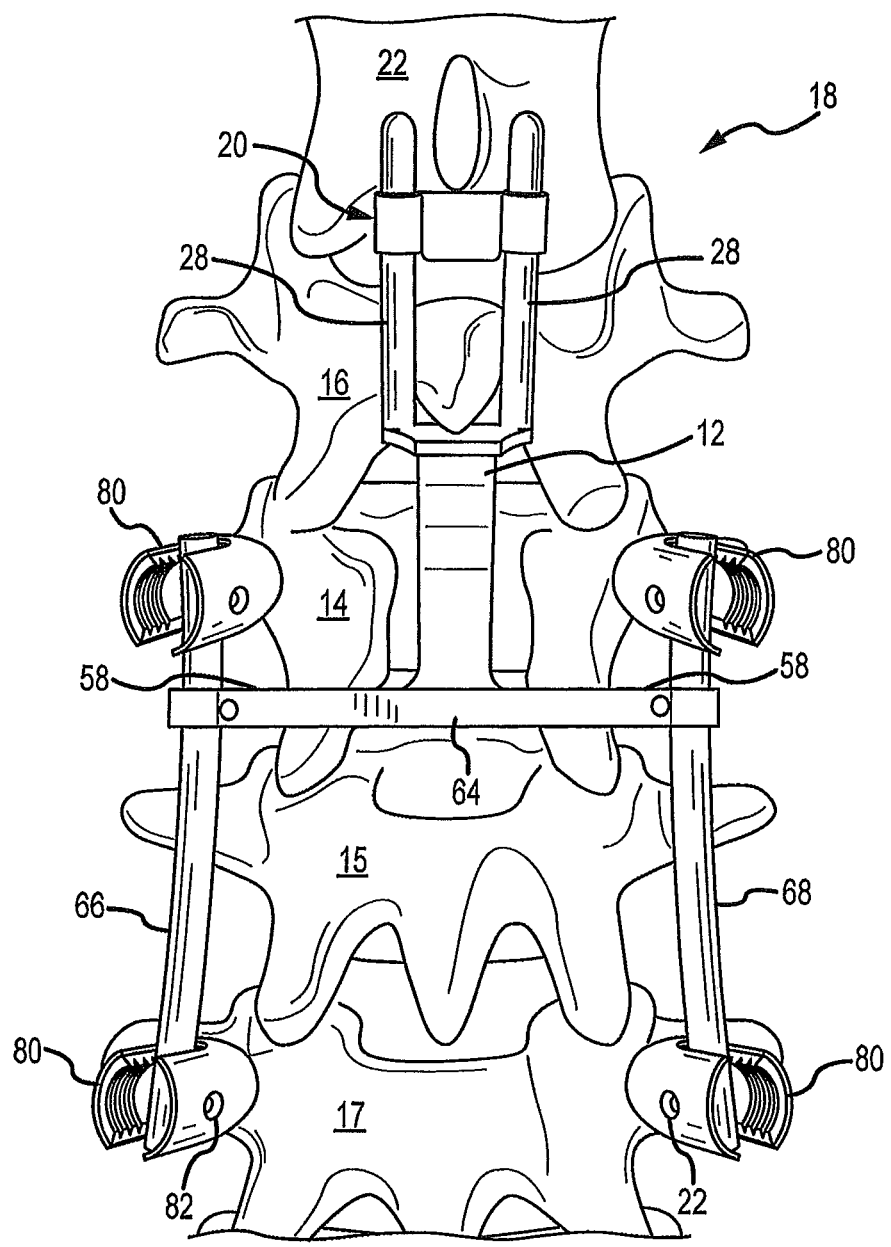
FIG. 10 is a front plan view of a spinal stabilization system of the present invention affixed to a spinal column.
Figure 11:
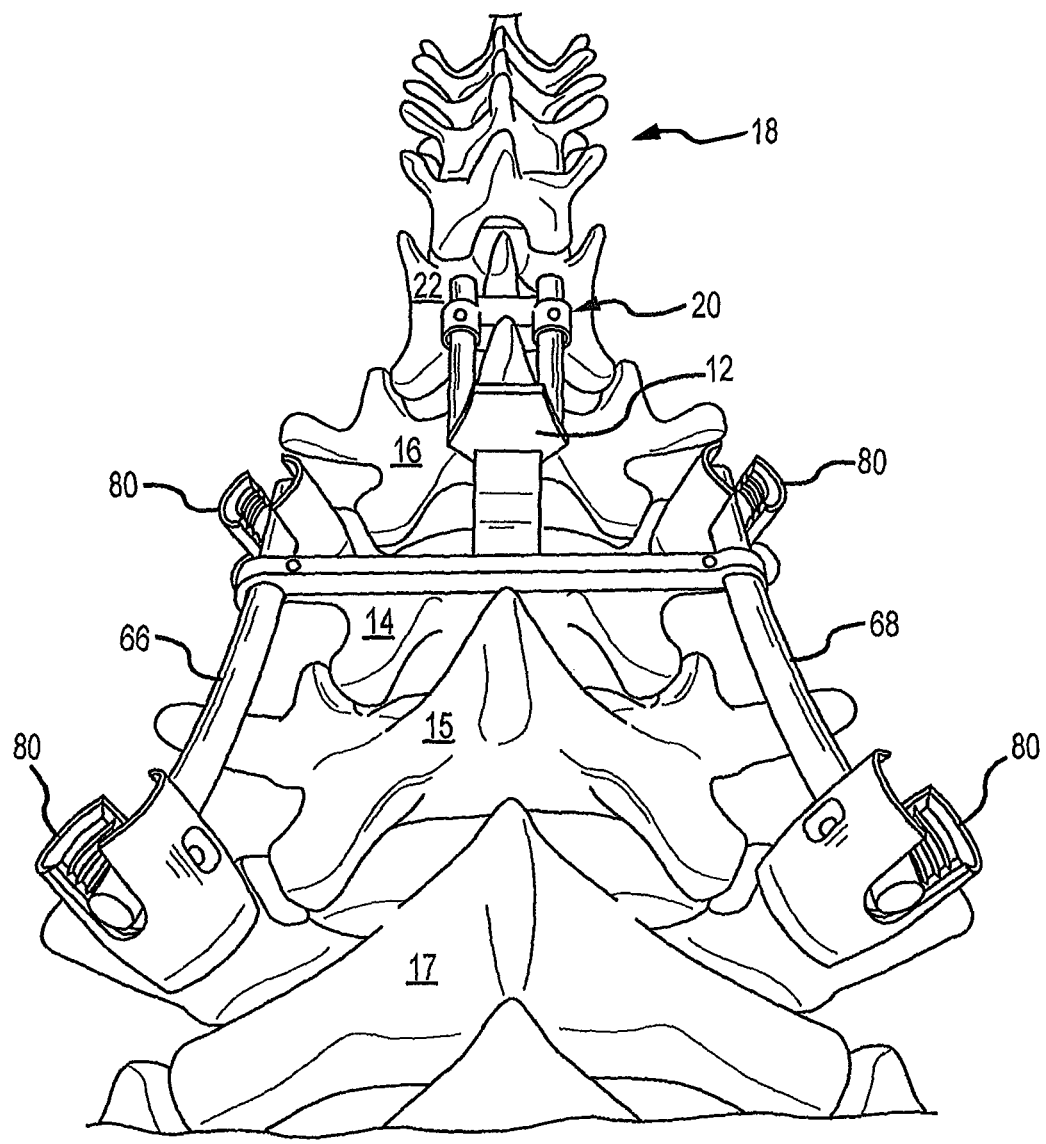
FIG. 11 is a bottom front perspective view of a spinal stabilization system of the present invention affixed to a spinal column.
Figure 12:
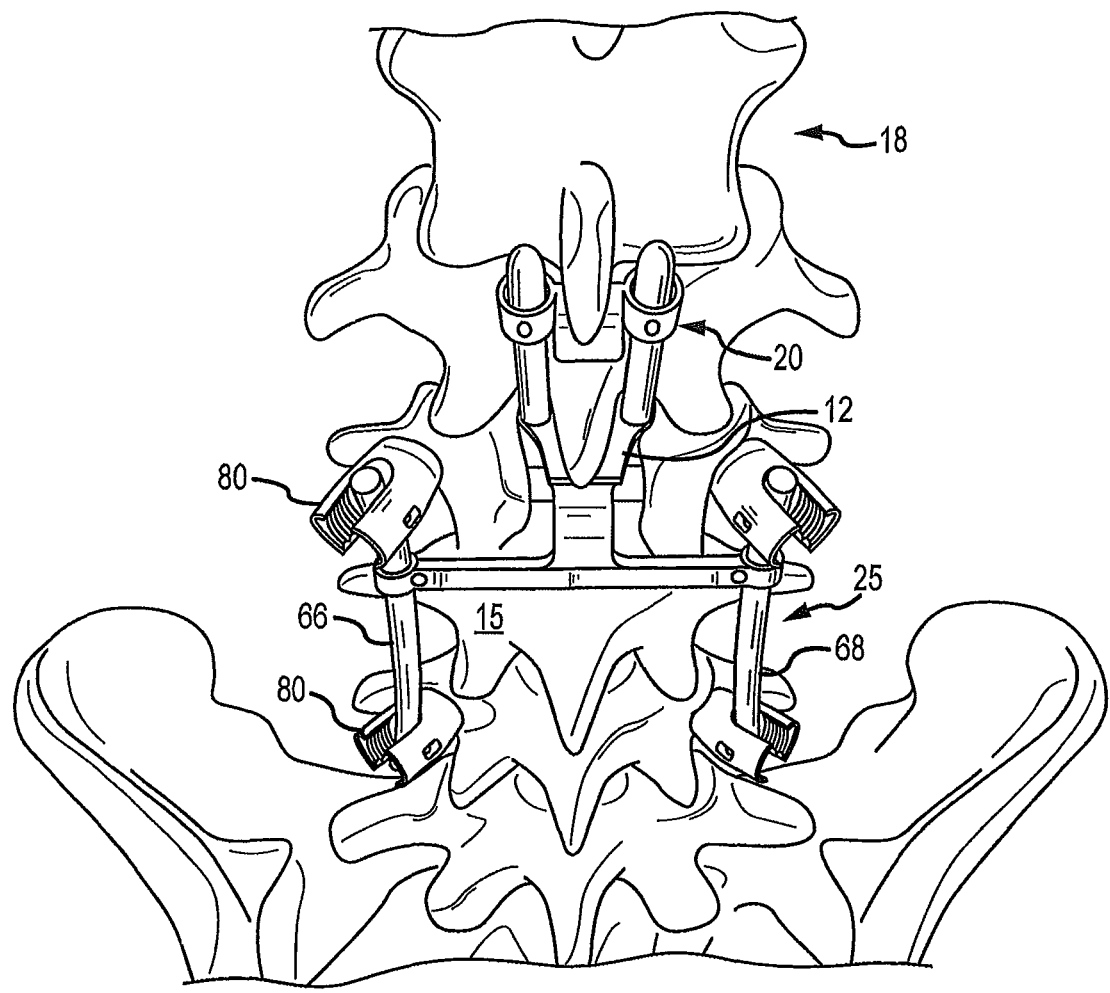
FIG. 12 is a top front perspective view of a spinal stabilization system of the present invention affixed to a spinal column.
Figure 13:
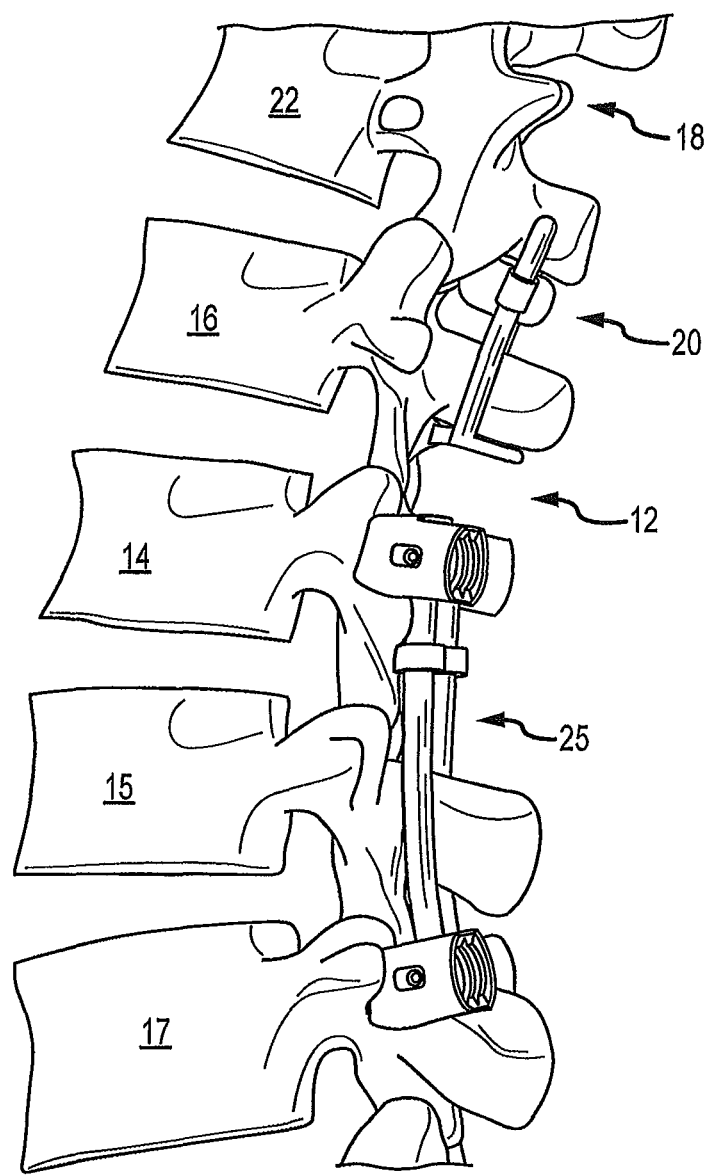
FIG. 13 is a side perspective view of a spinal stabilization system of the present invention affixed to a spinal column.

The support structure 25 comprises a pair of support members or guide rods 28 secured to the first interlaminar support member 12 and extending in a direction upwardly therefrom substantially parallel to one another. The second interlaminar member 20 includes a body portion 21 of a preselected thickness t, which is most clearly illustrated in FIG. 9. Thickness t is selected based upon the spacing between the second and third vertebrae and is intended to be smaller in size than the spacing to allow for flexion of the spinal column 18.

The body portion 21 further includes a pair of oppositely positioned ears 30 extending laterally outwardly from the body portion in opposing directions, each of the ears containing an aperture 32 structured and arranged to slideably receive one of the support members or guide rods 28. As will be discussed in greater detail below, the second interlaminar member is movably supported by upwardly extending support members or guide rods, and the position of the second interlaminar member 20 relative to the first interlaminar member 12 may be adjusted depending upon the dimensions of the specific spinal column on which the system is installed and the range of motion desired. Once the position of the second interlaminar member 20 has been selected, it is locked in place by a pair of set screws or other suitable fastening means 34 extending through each of the ears 30 and adapted to releaseably engage the respective guide rod extending therethrough.

Referring now to FIGS. 2, 3, 7 and 8, the first interlaminar member is 12 depicted in greater detail. The first interlaminar member comprises a U-shaped body 40 defined by an elastic midsection 42, two spaced apart end portions 44, and a pair of juxtaposed legs 46, each leg extending substantially parallel to one another from one of the respective ends in a direction generally outwardly away from the spinal column 18 (FIG. 7) and spaced apart a preselected distance d. Distance d is determined by the size of the first interlaminar member, which, in turn, is selected based upon the spacing between the first and second vertebrae. The first interlaminar member is intended to fuse the first and second vertebrae. Accordingly, it is sized to be a tight fit, and the elastic properties of the U-shaped body 40 act as a spring or shock absorber in the interface between the two vertebrae. Further, the uppermost one of the legs 46 is longer than the lower one of the legs, thereby forming a handle 48 which may be used to insert and position the system during surgery.

Referring again to FIG. 1, the support structure 25 further includes a T-shaped frame member 50 operatively connected to the first and second interlaminar members 12 and 20 and extends generally downwardly therefrom in a direction substantially parallel to the spinal column 18. The T-shaped frame member includes an elongate body 52 having first and second end portions 54, 56, the first end portion being operatively connected to the first interlaminar member 12, and an elongate cross member 58. The cross member has first and second end portions 60, 62 and a midpoint 64 and is structured and arranged to be connected to the second end portion 56 of the body 52 at approximately the midpoint 64. Each of the ends 60, 62 of the cross member 58 are adapted to receive and adjustably secure first and second support members 66 and 68 respectively. In the embodiment shown, each of the end portions 60, 62 have an aperture 70, 72 formed therein respectively for receiving one of the support members 66, 68, each of which may be held in a preselected position by a set screw 74.

In the embodiment shown, by way of example only and not of limitation, the support members are in the form of guide rods 66, 68, each guide rod having an upper end 76 and a lower end 78. Each of the upper and lower ends of the support members 66, 68 has a securing device 80 slideably positioned thereon and adapted to be secured thereto by means of set screws 82. By way of example, each of the securing devices is shown in the form of a pedicle screw 84, each pedicle screw being structured and arranged to be secured to one of the vertebra of the spinal column 18.

Figure 6:
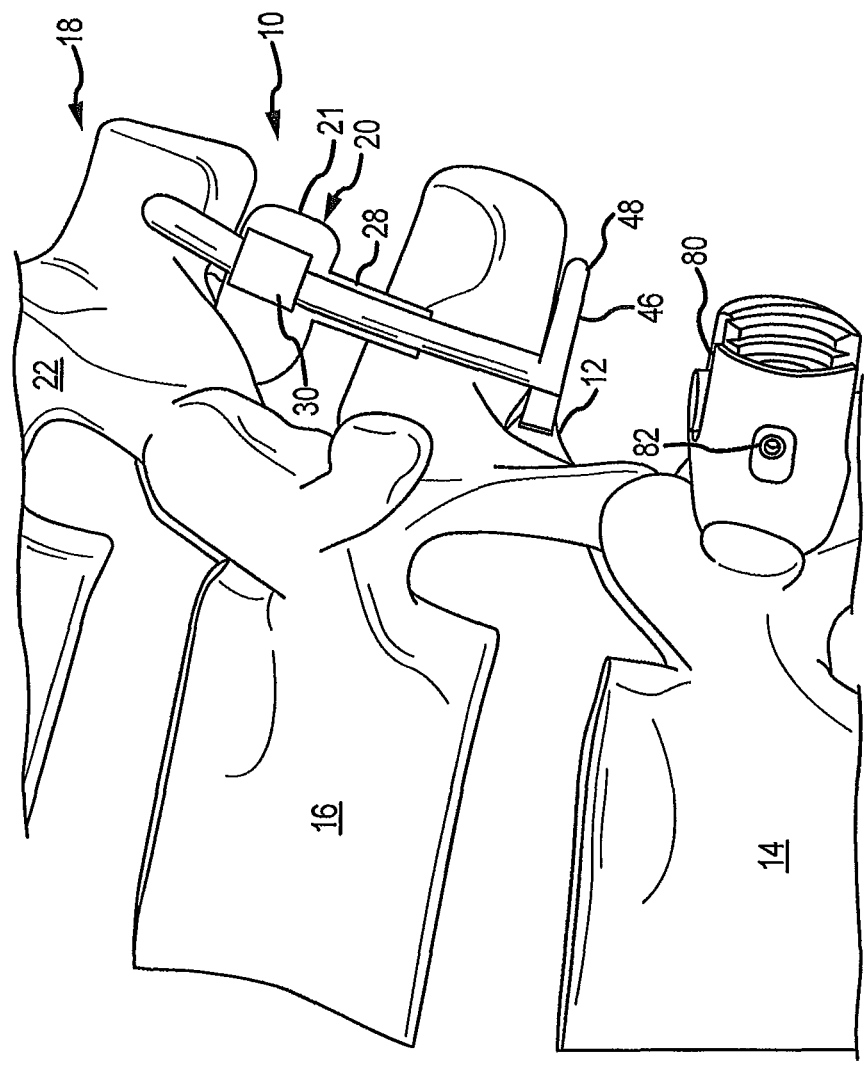
FIG. 6 is an enlarged side plan view of a portion of the spinal stabilization system of the present invention shown in FIG. 3 showing an upper portion of the stabilization system affixed to a spinal column.
Figure 7:
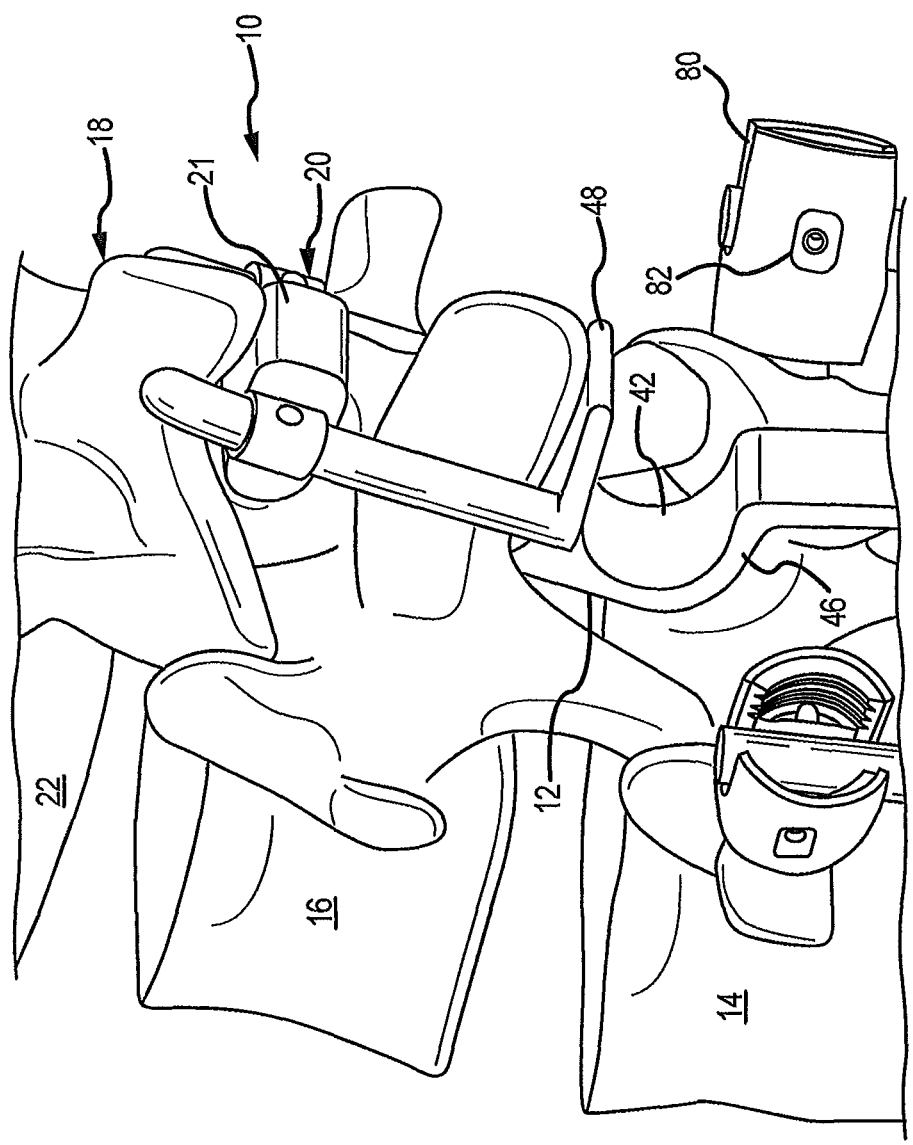
FIG. 7 is a side perspective view of a portion of the spinal stabilization system shown in FIG. 6.
Figure 8:
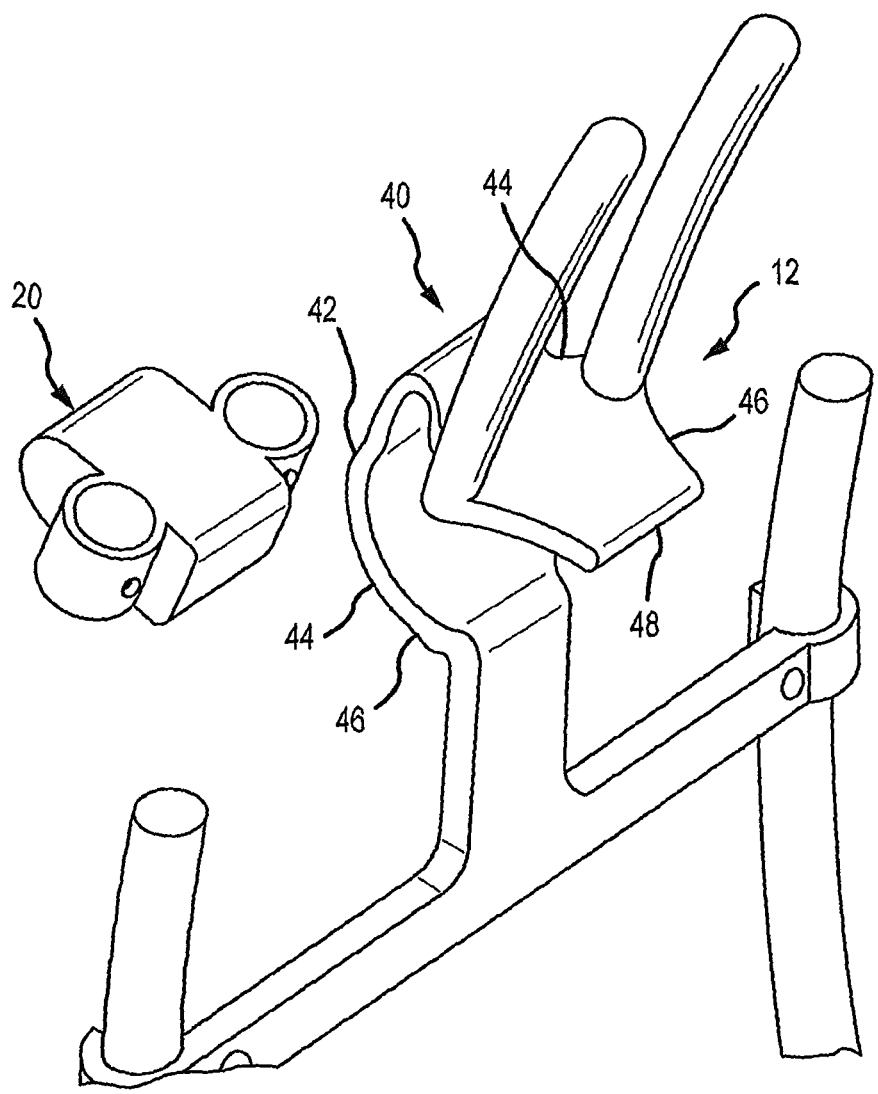
FIG. 8 is an exploded front perspective view of a portion of the spinal stabilization system shown in FIGS. 6 and 7.

The installation and operation of the spinal support system 10 of the present invention are illustrated in greater detail in FIGS. 6, 7, and 10-13. The system advantageously may be installed where other spinal fusion devices or similar medical apparatus are already in place to add stability to the spinal column above and below the installation point, to control flexion and/or rotational movement of the spine or selected vertebrae with respect to one another, and to prevent impingement of adjacent vertebrae, spinal processes, pedicle screws and medical hardware on one another. By way of example, as best shown in FIGS. 6 and 7, a surgeon may insert the system 25 into the space between adjacent vertebrae 14 and 16 by gripping handle 48 and making the insertion. The tight fitting U-shaped body 40 not only serves to control any motion between the adjacent vertebrae or even eliminate it entirely, thereby effectively fusing the vertebrae, but also serves as a dampening cushion or spring device by virtue of the spring-like elasticity of the body 40 translated to the vertebrae via legs 46. Thereafter, the second interlaminar member 20 may be selectively positioned intermediate vertebra 16 and vertebra 22 to permit flexion on a forward direction but to limit extension in the rearward direction and to limit compression of the spinal segment, thereby imparting enhanced stability to the spinal column above the fused vertebrae.

In a similar manner, support structure 25, via the T-shaped frame member 50 and support members or guide rods 66 and 68, provides support to the spinal processes located below the fused vertebrae 14 and 16. As shown in FIGS. 10-13, the pedicle screws 80 may be positioned in first vertebra 14 and in either vertebra 15 immediately adjacent to vertebra 14, or at a lower level as shown by vertebra 17, thus extending the stabilizing effect of the novel support system of the present invention to multiple levels in the spinal column 18. More than one level may be addressed simply by lengthening the rods 66 and 68 and slideably positioning multiple pedicle screws 80 thereon for selective positioning along the spinal column.

In one aspect, the cross member midpoint 64 may be configured, structured and arranged to be adjustably (e.g., pivotably or translatably) connected or secured to the second end portion 56 of the body 52 at approximately the midpoint 64 in order to allow a surgeon during the course of the surgical procedure to adjust and align components of the implant in relation to the patient's bony anatomy and in relation to support members 66 and 68.

In another aspect, elongate body 52 may be comprised of multiple pieces. For example, one or more linear racks may be configured in operable relation with gear mechanisms, thereby forming a ratchet device (not shown), in order to extend the distance between first and second end portions 54 and 56 thereby permitting a surgeon during the course of the surgical procedure to adjust and align components of the implant in relation to the patient's bony anatomy and subsequently securing them in place. For example, a ratchet mechanism configuration may permit the surgeon to progressively extend elements of the implant to better appose a lamina.

In yet another aspect, each of the ends 60, 62 of the cross member 58 may be configured to permit a degree of adjustability (e.g., pivotably or translatably) to receive and adjustably secure first and second support members 66 and 68 respectively. For example any cross-link variable adjustment mechanism or fastener known in the art may be employed to accomplish the desired fixation between the ends 60, 62 of the cross member 58 and first and second support members 66 and 68.

According to particular embodiments, interlaminar member 20 may be configured to permit connection to guide rods 28 via an approach that is substantially perpendicular to the longitudinal axis of guide rods 28. In other words, after the other components of the system have been implanted via a posterior approach to the posterior aspect of the spine, the interlaminar member 20 may follow a generally similar approach trajectory and then be secured to the guide rods 28 with, e.g., set screws in a similar manner to the engagement between the ends 60, 62 of the cross member 58 and first and second support members 66 and 68. Furthermore, in another aspect, an interlaminar member 20 may be used alone (and may alternatively be configured to be similar to the U-shaped body 40) and may be directly engaged with a first and second support members 66 and 68 and positioned between the lamina and spinous processes of the spine.

In particular aspects, the different elements of the system may be configured with tool engagement features in order to permit a surgeon to grasp the implant with a tool assembly or insertion tool to ease implantation of the various components. For example, the insertion tool may be configured as a pair of pliers or hemostats. As another example, a threaded portion of a tool assembly may reversibly secure to a complementary threaded portion of the implant in order to ease implantation. E.g., a tool assembly may be comprised of a cannulated shaft with a retainer shaft housed substantially within, the retainer shaft further configured with a threaded portion at its distal end which may extend out of a distal end of the retainer shaft and a handle located and attached to a proximal end of the retainer shaft; the distal end of the retainer shaft may have a feature that permits rotation of the retainer shaft via another tool, such as the mechanical arrangement that exists between a wrench and nut, in order to secure the tool assembly to the implant. After implantation of the implant the tool assembly may be decoupled and removed.

Changes may be made in the above methods and systems without departing from the scope hereof. It should thus be noted that the matter contained in the above description and/or shown in the accompanying figures should be interpreted as illustrative and not in a limiting sense. The following claims are intended to cover all generic and specific features described herein, as well as all statements of the scope of the present systems and methods, which, as a matter of language, might be said to fall there between.

What is claimed is:

1. A spinal stabilization system for treating a spinal column having a first vertebra and a second vertebra, the system comprising:
   an interlaminar member adapted to be positioned between the first vertebra and the second vertebra; the interlaminar member including a U-shaped body having a midsection, and two spaced apart end portions, and a pair of juxtaposed legs extending substantially parallel to one another from the U-shaped body, each of the pair of juxtaposed legs having a first end connected to one of the two respective spaced apart end portions of the U-shaped body, each leg including a second end located opposite the first end;

a support structure operatively connected to the interlaminar member, the support structure including a T-shaped frame member operatively connected to the interlaminar member and extending generally downwardly therefrom, the T-shaped frame member including an elongate body having first and second end portions, the first end portion of the elongate body being operatively connected to the interlaminar member at the second end of one of the pair of juxtaposed legs, and an elongate cross member having first and second end portions and a midpoint, the elongate cross member being operatively connected approximately at the midpoint to the second end portion of the elongate body.

2. The system of claim 1 further including first and second guide rods adjustably secured to the first and second ends of the elongate cross member respectively.

3. The system of claim 2 where each of the first and second guide rods includes an upper and a lower end, each of the upper and lower ends having a securing device slideably positioned thereon, each securing device being structured and arranged to be secured to a vertebra in the spinal column.

4. The system of claim 2, wherein each of the first and second end portions of the elongate cross member further includes an aperture formed therein configured to pivotably and/or translatably receive a respective one of the first and second guide rods and a fastener adapted to the respective one of the first and second guide rods in a preselected position.

5. The system of claim 1, wherein the elongate body includes at least one linear rack, the rack being structured and arranged to progressively extend the distance between the first and second end portions of the elongate body of the T-shaped frame member.

6. The system of claim 5, further including a gear mechanism operatively connected to the at least one linear rack, the gear mechanism and the at least one linear rack forming a ratchet device configured to permit the progressive extension.

7. The system of claim 1 wherein the support structure includes a pair of support members secured to the interlaminar member at one of the pair of juxtaposed legs, the leg being opposite the leg to which the elongate body is attached, the support members extending upwardly therefrom in a direction substantially parallel to one another.

8. The system of claim 1 wherein the interlaminar member is structured and arranged to fit tightly between the first vertebra and the second vertebra.

9. The system of claim 1, wherein the midsection is elastic.

10. The system of claim 1, wherein the support structure and the interlaminar member are integrally formed from a single piece of material.

11. A system for treating a patient's spinal column, the system comprising:

a spinal stabilization system including an interlaminar member adapted to be positioned between a first vertebra and a second vertebra in a spinal column; the interlaminar member including a U-shaped body having a midsection, and two spaced apart end portions, and a pair of juxtaposed legs extending substantially parallel to one another from one of the respective ends in a direction generally outwardly away from the spinal column;

a support structure operatively connected to the interlaminar member and adapted to be connected to the first vertebra and at least one vertebra positioned below the first vertebra in the spinal column, the support structure including a T-shaped frame member operatively connected to the interlaminar member and extending generally downwardly therefrom in a direction substantially parallel to the direction of the spinal column, the T-shaped frame member including an elongate body having first and second end portions, the first end portion being operatively connected to the interlaminar member, and an elongate cross member having first and second end portions and a midpoint, the elongate cross member being operatively connected approximately at the midpoint to the second end portion of the body and an insertion tool configured to reversibly secure to a tool engagement portion of the spinal stabilization system, the insertion tool being adapted to permit a surgeon to grasp the system with the insertion tool whereby implantation of the system in the patient's spinal column is facilitated.

12. The system of claim 11, wherein the insertion tool comprises a pair of pliers or hemostats.

13. The system of claim 12, wherein the tool engagement portion includes a threaded portion and wherein the insertion tool includes a threaded portion configured to reversibly secure to the threaded portion of the tool engagement portion of the spinal stabilization system.

14. The system of claim 13, wherein the insertion tool includes a cannulated shaft and a retainer shaft housed substantially within the cannulated shaft, the retainer shaft including a distal end and a proximal end opposite the distal end, the distal end of the retainer shaft comprising the threaded portion thereof and the proximal end of the retainer shaft comprising a handle.

15. A spinal stabilization system comprising: an interlaminar member adapted to be positioned between a first vertebra and a second vertebra in a spinal column; the interlaminar member including a U-shaped body having a midsection, and two spaced apart end portions, and a pair of juxtaposed legs extending substantially parallel to one another from one of the respective ends in a direction generally outwardly away from the spinal column; a support structure operatively connected to the interlaminar member, the first vertebra and at least one vertebra positioned below the first vertebra in the spinal column, the support structure including a T-shaped frame member operatively connected to the interlaminar member and extending generally downwardly therefrom in a direction substantially parallel to the direction of the spinal column, the T-shaped frame member including an elongate body having first and second end portions, the first end portion being operatively connected to the interlaminar member, and an elongate cross member having first and second end portions and a midpoint, the elongate cross member being operatively connected approximately at the midpoint to the second end portion of the body; wherein the pair of juxtaposed legs comprises an uppermost leg and a lowermost leg, the first end portion of the elongate body being operatively connected to the interlaminar member at the lowermost leg and wherein the uppermost leg is longer that the lowermost leg.

16. The system of claim 15, wherein the uppermost leg forms a handle adapted to facilitate insertion and positioning of the system during surgery.

17. A spinal stabilization system for treating a spinal column having a first vertebra and a second vertebra positioned adjacent the first vertebra, the system comprising: an interlaminar member adapted to be positioned between the first vertebra and the second vertebra; the interlaminar member including a U-shaped body having a midsection, and two spaced apart end portions, and a pair of juxtaposed legs, each leg having a first end connected at each spaced apart end portion, respectively, and extending generally parallel to one another from each one of the respective ends and each leg having a second end opposite the first end; a support structure operatively connected to the interlaminar member, the support structure including a T-shaped frame member operatively connected to the interlaminar member and extending generally downwardly therefrom, the T-shaped frame member including an elongate body having first and second end portions, the first end portion of the elongate body being operatively connected to the interlaminar member, and an elongate cross member having first and second end portions and a midpoint, the elongate cross member being operatively connected approximately at the midpoint to the second end portion of the body of the elongate body;

wherein the T-shaped frame is defined by a first plane, the U-shaped body is defined in a second plane and wherein an arrangement between the T-shaped frame and U-shaped body is such that the first plane is generally perpendicular to the second plane.

\* \* \* \* \*